United States Patent [19]

King

[11] Patent Number: 5,733,241
[45] Date of Patent: Mar. 31, 1998

[54] FIBEROPTIC INTUBATION STYLET

[76] Inventor: George Hwa Kou King, 30452 Via Rivera, Rancho Palos Verdes, Calif. 90275

[21] Appl. No.: 595,194

[22] Filed: Feb. 1, 1996

[51] Int. Cl.⁶ .................................................. A61B 1/04
[52] U.S. Cl. ........................ 600/114; 600/121; 600/125; 600/144
[58] Field of Search .................................. 600/114, 115, 600/120, 121, 122, 123, 124, 125, 139, 144, 146, 186, 194, 203; 128/200.26; 604/263

[56] References Cited

U.S. PATENT DOCUMENTS

| 4,886,049 | 12/1989 | Darras | 600/123 X |
| 5,025,778 | 6/1991 | Silverstein et al. | 600/144 X |
| 5,197,457 | 3/1993 | Adair | 600/121 X |
| 5,237,984 | 8/1993 | Williams, III et al. | 600/124 |
| 5,325,845 | 7/1994 | Adair | 128/4 |

*Primary Examiner*—Beverly M. Flanagan
*Attorney, Agent, or Firm*—David & Raymond; Raymond Y. C. Chan

[57] ABSTRACT

A fiberoptic intubation stylet is an endotracheal intubation aid for use with a fiberoptic scope to facilitate difficult endotracheal intubations particularly when a direct line of sight is not available due to patient's anatomy or pathology. The fiberoptic intubation stylet comprises a pre-sterilized soft transparent plastic holding sheath with a longitudinally built-in malleable metal stylet. The tubular holding sheath provides a neat and secure contact of the fiberoptic scope so that the stylet can be held in position. The malleable stylet makes the fiber optic scope as firm and able to be curled into a shape of an ordinary intubation stylet that is familiar to all intubators, thus enableing the fiberoptic scope to be manipulated as an ordinary intubation style in any clinical situation, even when a direct line of sight is not possible. Since the holding sheath can sufficiently cover the total intraoral portion of a fiberoptic scope, it protects the scope from contacting the patient and prevents contamination. The scope thus needs not be sterilized after each use and can be used in other patient without delay. This feature not only increases the efficiency of the scope usage but also reduces the expansion for sterilization and repair, as well as prolonging the life of the scope, which is very delicate and expensive. The present invention thus provides not only a convenient and efficient alternative to conventional fiberoptic intubation technology that also has great promise as a major advancement in airway management, but its low cost shall also play a very important role in the new realities of today's healthcare industry.

20 Claims, 6 Drawing Sheets

FIBEROPTIC INTUBATION STYLET

BACKGROUND OF THE INVENTION

The present invention relates to an instrument for facilitating endotracheal intubation, and more particularly to a fiberoptic intubation stylet equipped with a fiberoptic scope for difficult intubations.

Endotracheal intubation, placement of a tube into the trachea, is the most rapid and usually the easiest method to ensure a patent airway. It has, therefore, earned its popularity in anesthesia practice as well as in emergency medicine and intensive care units/areas. The advantages of endotracheal intubation are many. Since patency of the airway is assured, aspiration is prevented and secretions may be removed with relative ease from the tracheobronchial tree. Positive pressure ventilation, either manual or mechanical, can be applied to the airway for better control of ventilation and oxygen supply. Endotracheal intubation, therefore, is an integral part of airway management in modern-day medical practice. It has the first priority and plays a vital role in unconscious patients, patients under or emerging from general anesthesia, victims requiring acute resuscitation, and various patients needing chronic or critical intensive medical care.

However, establishing a patent airway by endotracheal intubation is not always attainable, particularly when trying to intubate a paralyzed patient where technical difficulties prevent this. Airway obstruction during the induction of general anesthesia, therefore, remains a persistent problem in modern anesthesia practice, especially in obstetric patients and those patients who have anatomical or pathological abnormalities. Failure to maintain a patent airway for more than a few minutes will result in brain damage or death. Thus, it is not surprising that more than 85 percent of all respiratory-related closed malpractice claims involve a brain-damaged or dead patient, and it has been established that inability to successfully manage very difficult airways has been responsible for as many as 30 percent of deaths totally attributable to anesthesia.

DESCRIPTION OF THE PRIOR ART

In cases requiring endotracheal intubation, traditionally a rigid laryngoscope is used for direct visualization of the glottis and vocal cords. The laryngoscope blades may be straight or curved. Nonetheless, the direct line of sight is always straight and must not be blocked. When patient's anatomy or pathology prevents direct visualization of the glottis and vocal cords, a flexible fiberoptic scope is generally the choice. However, fiberoptic-aided intubation is only useful in cooperative patients with spontaneous breathing. Additionally, because the view field and the range of motion of a fiberoptic scope are very limited, it therefore requires expertise to operate and is usually time consuming. Oftentimes, positioning the fiberoptic scope for viewing the larynx can be very difficult or even impossible, particularly when there is a large floppy epiglottis. Several aids have been described, but none has the flexibility and maneuverability as well as the simplicity, easiness and cost effectiveness as the present invention.

SUMMARY OF THE INVENTION

The main object of the present invention is to provide an endotracheal intubation aid which can be effectively attached to a fiberoptic scope to make it as firm as an ordinary intubation stylet.

Another object of the present invention is to provide an endotracheal intubation aid which can be effectively attached to a fiberoptic scope and to be curled into a shape of an ordinary intubation stylet, that is familiar to all intubators, for easy handling and fast operation.

Another object of the present invention is to provide an endotracheal intubation aid which has a pre-sterilized plastic holding sheath that can neatly and sufficiently cover the total intraoral portion of a fiberoptic scope in order to protect the scope from contacting the patient, therefore, prevents contamination and needs not be sterilized after each use, thus, permits the scope to be used in other patient without delay.

Accordingly, the present invention is an one-time use disposable device, made of non-toxic material, comprising a plastic holding sheath and a malleable metal stylet which is integrally built in the plastic holding sheath. The plastic holding sheath is adapted to secure the stylet in the operation position and to protect the scope from contamination during the intubation procedure. The malleable metal stylet makes the fiberoptic scope as firm and maneuverable as an ordinary intubation stylet for easy handling and high efficiency.

The present invention can be manufactured in different sizes to adapt different fiberoptic scopes made by different manufacturers as well as for different patient sizes.

Due to the flexibility and the miniature size of the stylet, the present invention can be closely secured to a fiberoptic scope and to be inserted together with the fiberoptic scope into the lumen of an endotracheal tube, thus, enables the fiberoptic scope to be manipulated as an ordinary intubation stylet in any clinical situation, even when a direct line of sight is not possible due to patient's anatomy or pathology. Due to the non-toxic nature and the smooth soft surface of the plastic holding sheath, it, therefore, will not irritate and/or traumatize the oropharyngeal tissues. Furthermore, since the device is supplied pre-sterilized and the holding sheath covers the total intra-oral portion of the fiberoptic scope it prevents contamination and permits the scope to be used in another patient without delay. This feature not only increases the efficiency of the scope usage but also reduces the expenses for sterilization and repair, as well as prolonging the life of the scope which is very delicate and expensive.

The herein described present invention provides a convenient and inexpensive alternative to conventional fiberoptic intubation technology. It has a great promise as a major advancement in airway management. Additionally, its competitive cost effectiveness shall play a very important role in the new realities of today's healthcare industry.

DETAILED DESCRIPTION OF THE INVENTION

Figure 1:
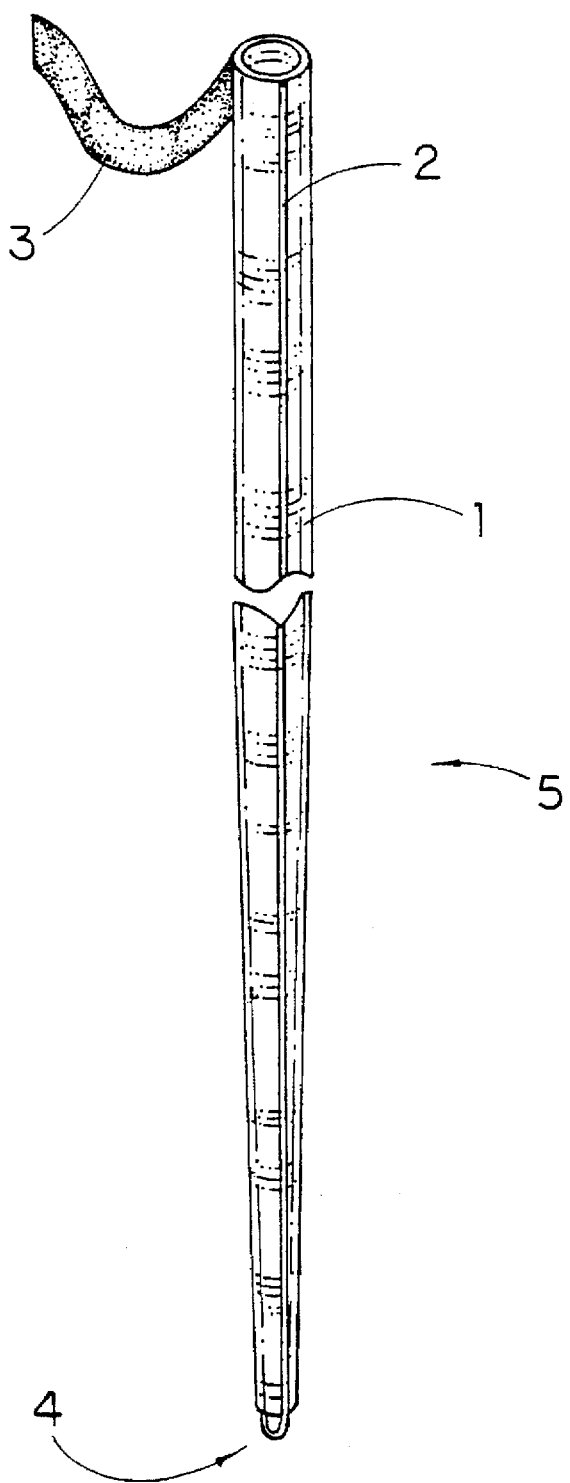
FIG. 1 is a perspective view of a preferred embodiment according to the present invention.
Figure 2:
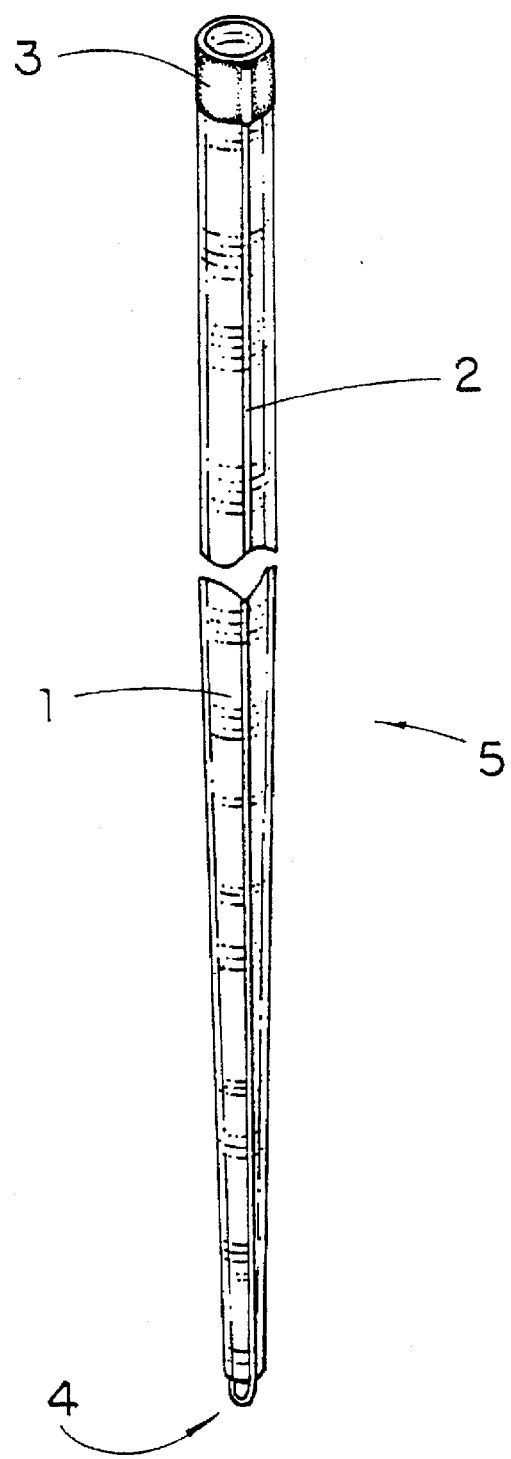
FIG. 2 is a plane view of the above preferred embodiment equipped with a fiberoptic scope according to the present invention.
Figure 3:
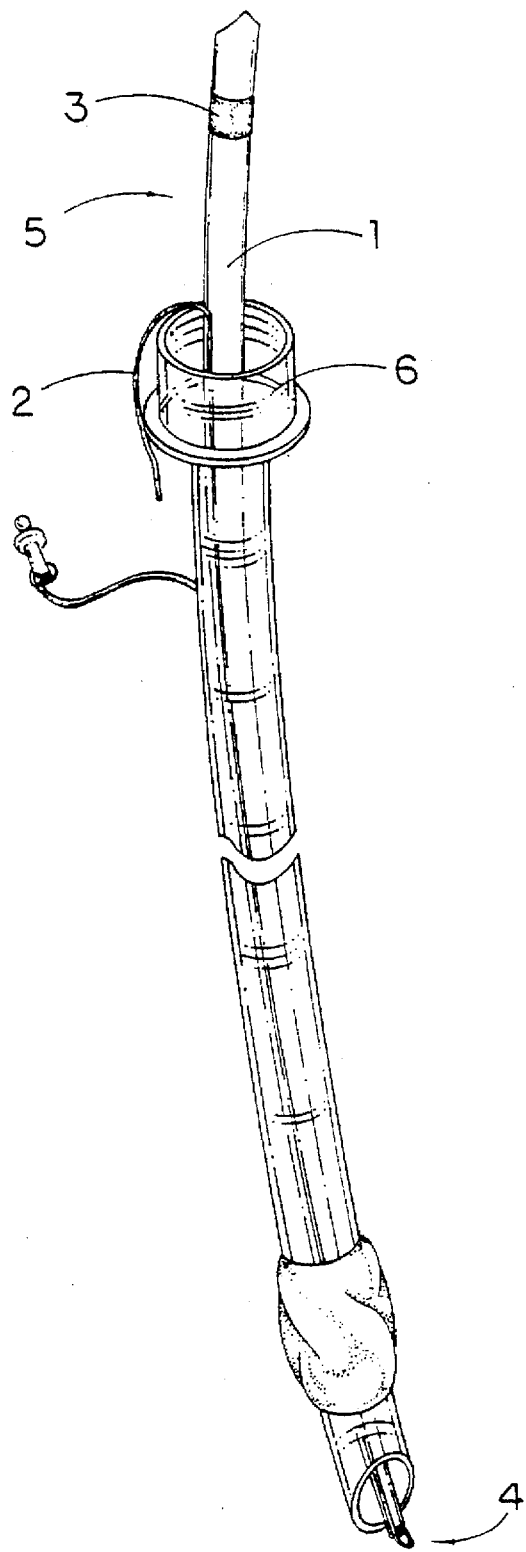
FIG. 3 is a perspective view of the above preferred embodiment equipped with a fiberoptic scope which is inserted into the lumen of an endotracheal robe according to the present invention.
Figure 4:
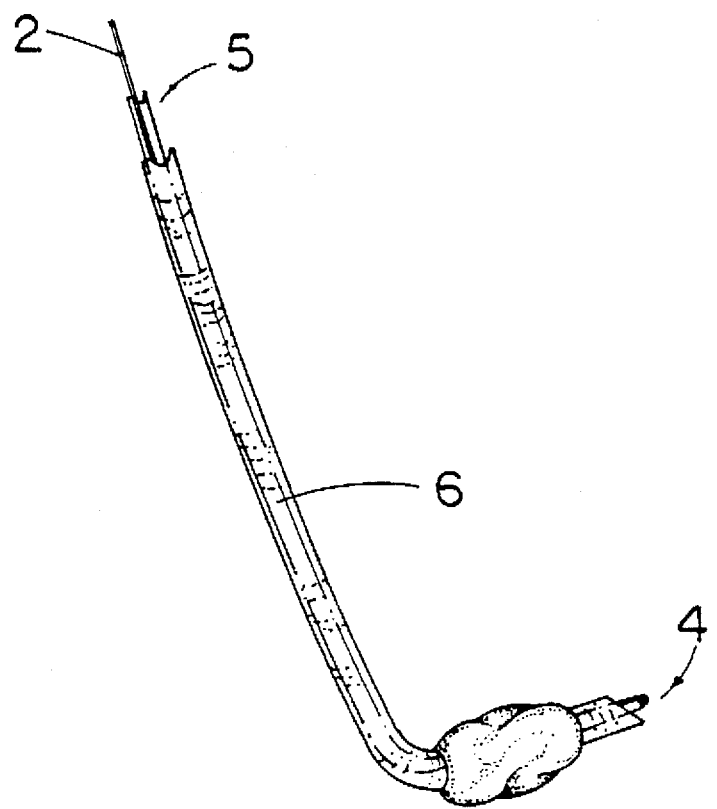
FIG. 4 is a plane view of the above preferred embodiment equipped with a fiberoptic scope which is inserted into the lumen of an endotracheal tube and curled into J-shape ready for intubation according to the present invention.
Figure 5:
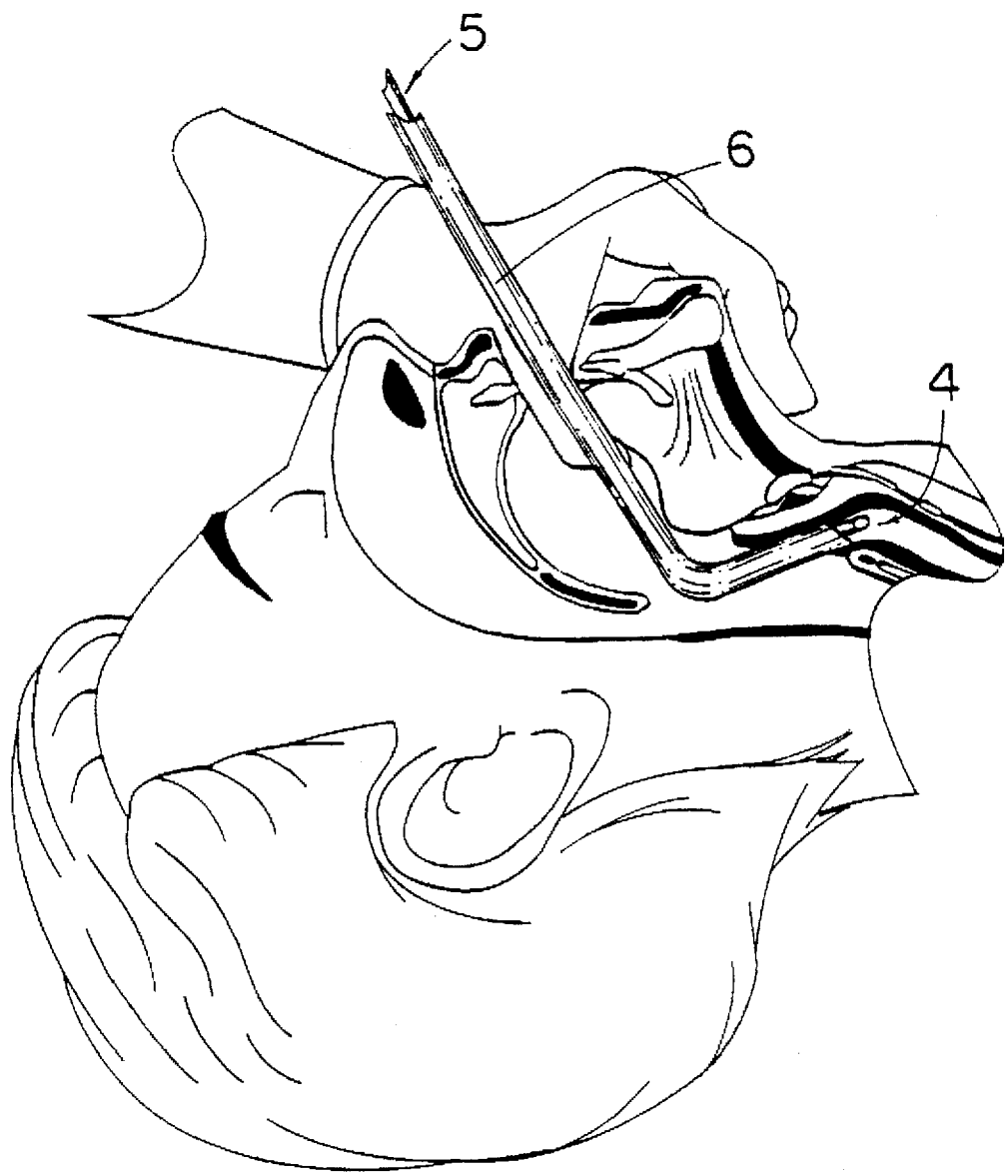
FIG. 5 is a partial sectional view showing the present invention as used in oral endotracheal intubation.

Referring to FIGS. 1 to 5 and more specifically to FIG. 1, a disposable fiberoptic intubation stylet, made of nontoxic materials, comprises a tubular plastic holding sheath 1 as a holding means, and a longitudinally built-in narrow malleable metal intubation stylet 2 which is narrow piece of flat metal built into the holding sheath and is adhered to an outer wall of the holding sheath. The plastic holding sheath is transparent in nature in order to provide a clear visualization of the anatomy. A first end of the transparent and soft plastic holding sheath 1 is opened and comprises an adhesive backed holding strap 3, which is a plastic holding strap attached transversely at the edge of the first opened end of the holding sheath 1 so as to encircle a fiberoptic scope 5 in order to hold the device firmly to the fiberoptic scope 5 at its operating position (as shown in FIG. 2 and 3). A second end of the plastic holding sheath 1 is tapped to form a small point 4 for neatly accommodating: the tip of the fiberoptic scope 5 (as shown in FIG. 2). The metal intubation stylet 2 is integrally longitudinally extended along and outside the plastic holding sheath 1 and is malleable so that the fiberoptic intubation stylet can be curled to a shape of an ordinary intubation stylet (as shown in FIG. 4). Referring to FIG. 3, the proximal portion of the metal stylet 2 is peeled off from the plastic holding sheath 1 and bent over an endotracheal robe 6 to regulate the length of the stylet 2 and the fiberoptic scope 5 to be introduced through the endotracheal tube 6 as well as to secure it in position as a holding means to the endotracheal tube 6. The tubular plastic holding sheath 1 has a length enough to cover the total intraoral portion of the fiberoptic scope 5 in order to protect the scope from contacting the patient and subsequently preventing contamination.

Figure 6:
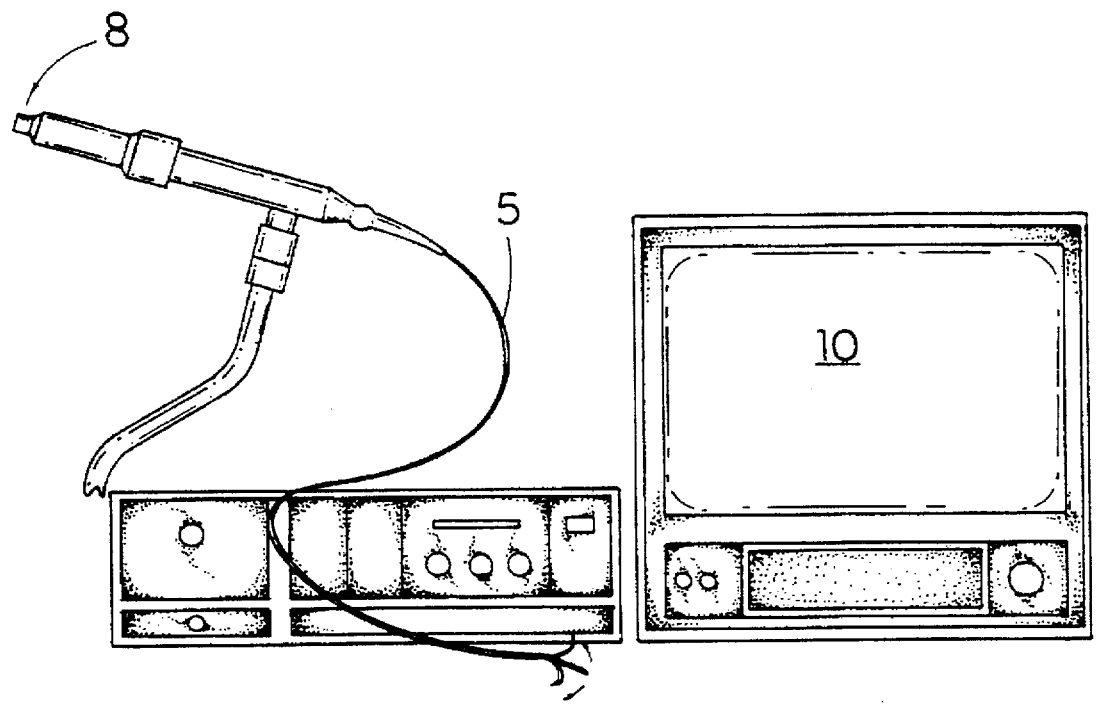
FIG. 6 is an illustrating view of a conventional fiberoptic scope, illuminator and video monitor setup.

The outer aspect surface of the plastic holding sheath 1 which overs the intraoral portion of the fiberoptic scope 5 is lubricated and inserted together with the fiberoptic scope 5 into the lumen of the predetermined endotracheal tube 6 (as shown in FIG. 3). A laryngoscope may be used to displace the tongue and soft tissues and/or for identification of the macroanatomy of the oral cavity in order to facilitate positioning the tip of the fiberoptic scope 5 for best viewing of the glottis and the vocal cords. The intubator can view the anatomy of the larynx either through an eye piece 8 of the fiberoptic scope 5 (as shown in FIG. 6) or the image being transmitted to a video monitor 10. When necessary, intubation is reshaped stylet 2 according to the individual anatomy/pathology. The tip of the fiberoptic scope 5 is gently inserted and the endotracheal is slid tube between the vocal cords into the larynx, then into the trachea of the patient in an usual manner.

The equipment and procedure as described above have many advantages over other devices and methods. It has the advantages of both direct laryngoscopic and fiberoptic intubations. A laryngoscope can be used to identify the oral macroanatomy to facilitate rapid positioning of the fiberoptic scope. The fiberoptic scope 5 enables the visualization of the larynx when a straight, direct line of sight is not available due to the patient's anatomy or pathology. Since the size, shape and firmness of the device is similar to that of an ordinary intubation stylet, it can be handled the same way as an ordinary intubation stylet, and thus, no training is needed. Other advantages of present invention include its low cost nature that shall play a very important role in today's healthcare environment.

I claim:

1. A fiberoptic intubation stylet apparatus, comprising:
   a holding element which comprises a soft plastic holding sheath and a holding strap attached to a first end of said holding sheath for firmly fastening a fiberoptic scope thereto, wherein said holding sheath is in a tubular form and said first end is an opened end for accommodation of said fiberoptic scope; and
   a malleable intubation stylet, which is longitudinally extended along and outside said holding sheath, being built into an outer wall of said holding sheath in order to enable said holding sheath being curled to a predetermined shape.

2. A fiberoptic intubation stylet apparatus, as recited in claim 1, wherein said holding sheath has a tapped second end for tightly fitting to a tip of said fiberoptic scope.

3. A fiberoptic intubation stylet apparatus, as recited in claim 1, wherein said holding sheath has a length enough to cover a total intraoral portion of said fiberoptic scope in order to protect said fiberoptic scope from contacting a patient and subsequently preventing contamination.

4. A fiberoptic intubation stylet apparatus, as recited in claim 2, wherein said holding sheath has a length enough to cover a total intraoral portion of said fiberoptic scope in order to protect said fiberoptic scope from contacting a patient and subsequently preventing contamination.

5. A fiberoptic intubation stylet apparatus, as recited in claim 2, wherein said holding sheath is transparent in nature in order to provide a clear visualization of an anatomy of said patient.

6. A fiberoptic intubation stylet apparatus, as recited in claim 1, wherein said holding strap is a plastic holding strap for fastening to said fiberoptic scope.

7. A fiberoptic intubation stylet apparatus, as recited in claim 6, wherein said holding strap is positioned transversely at an edge of said first end in order to encircle said fiberoptic scope.

8. A fiberoptic intubation stylet apparatus, as recited in claim 7, wherein said holding strap is adhered on said fiberoptic scope in order to firmly fasten to said fiberoptic scope.

9. A fiberoptic intubation stylet apparatus, as recited in claim 4, wherein said holding strap is a plastic holding strap for fastening to said fiberoptic scope.

10. A fiberoptic intubation stylet apparatus, as recited in claim 9, wherein said holding strap is positioned transversely at an edge of said first end in order to encircle said fiberoptic scope.

11. A fiberoptic intubation stylet apparatus, as recited in claim 10, wherein said holding strap is adhered on said fiberoptic scope in order to firmly fasten to said fiberoptic scope.

12. A fiberoptic intubation stylet apparatus, as recited in claim 1, wherein said intubation stylet is a narrow piece of flat metal.

13. A fiberoptic intubation stylet apparatus, as recited in claim 4, wherein said intubation stylet is a narrow piece of flat metal.

14. A fiberoptic intubation stylet apparatus, as recited in claim 11, wherein said intubation stylet is a narrow piece of flat metal.

15. A fiberoptic intubation stylet apparatus, as recited in claim 1, wherein said intubation stylet is adhered to said outer wall of said holding sheath and that a proximal portion of said intubation stylet is peeled off from said holding sheath to bend over an endotracheal tube to hold said endotracheal tube in position and to regulate an amount of said intubation stylet and said fiberoptic scope to be introduced through said endotracheal tube.

16. A fiberoptic intubation stylet apparatus, as recited in claim 6, wherein said intubation stylet is adhered to said outer wall of said holding sheath and that a proximal portion of said intubation stylet is peeled off from said holding sheath to bend over an endotracheal tube to hold said endotracheal tube in position and to regulate an amount of said intubation stylet and said fiberoptic scope to be introduced through said endotracheal tube.

17. A fiberoptic intubation stylet apparatus, as recited in claim 5, wherein said intubation stylet is adhered to said outer wall of said holding sheath and that a proximal portion of said intubation stylet is peeled off from said holding sheath to bend over an endotracheal tube to hold said endotracheal tube in position and to regulate an amount of said intubation stylet and said fiberoptic scope to be introduced through said endotracheal tube.

18. A fiberoptic intubation stylet apparatus, as recited in claim 8, wherein said intubation stylet is adhered to said outer wall of said holding sheath and that a proximal portion of said intubation stylet is peeled off from said holding sheath to bend over an endotracheal tube to hold said endotracheal tube in position and to regulate an amount of said intubation stylet and said fiberoptic scope to be introduced through said endotracheal tube.

19. A fiberoptic intubation stylet apparatus, as recited in claim 11, wherein said intubation stylet is adhered to said outer wall of said holding sheath and that a proximal portion of said intubation stylet is peeled off from said holding sheath to bend over an endotracheal tube to hold said endotracheal tube in position and to regulate an amount of said intubation stylet and said fiberoptic scope to be introduced through said endotracheal tube.

20. A fiberoptic intubation stylet apparatus, as recited in claim 14, wherein said intubation stylet is adhered to said outer wall of said holding sheath and that a proximal portion of said intubation stylet is peeled off from said holding sheath to bend over an endotracheal tube to hold said endotracheal tube in position and to regulate an amount of said intubation stylet and said fiberoptic scope to be introduced through said endotracheal tube.

* * * * *